United States Patent
Dickson et al.

(10) Patent No.: US 8,992,525 B2
(45) Date of Patent: Mar. 31, 2015

(54) SURGICAL INSTRUMENT

(71) Applicant: ENT Biotech Solutions, Inc., Grosse Pointe Farms, MI (US)

(72) Inventors: Clark B. Dickson, Grosse Pointe Farms, MI (US); Gene P. Parunak, Saline, MI (US)

(73) Assignee: ENT Biotech Solutions, Inc., Grosse Pointe Farms, MI (US)

( * ) Notice: Subject to any disclaimer, the term of this patent is extended or adjusted under 35 U.S.C. 154(b) by 0 days.

(21) Appl. No.: 14/254,404

(22) Filed: Apr. 16, 2014

(65) Prior Publication Data

US 2015/0038964 A1 Feb. 5, 2015

Related U.S. Application Data

(60) Provisional application No. 61/860,905, filed on Jul. 31, 2013.

(51) Int. Cl.
*A61B 18/14* (2006.01)
*A61B 18/08* (2006.01)
*A61B 18/00* (2006.01)

(52) U.S. Cl.
CPC ..... *A61B 18/085* (2013.01); *A61B 2018/00327* (2013.01); *A61B 2018/00595* (2013.01)
USPC .............................................. 606/45; 606/41

(58) Field of Classification Search
CPC ................... A61B 17/28; A61B 17/29; A61B 2017/2808–2017/2948; A61B 2018/1407; A61B 2018/146; A61B 2018/1462; A61B 18/1442–18/1445
USPC .................... 606/27, 34, 41, 51, 52
See application file for complete search history.

(56) References Cited

U.S. PATENT DOCUMENTS

| 3,353,531 A | | 11/1967 | Armao |
| 5,396,900 A | * | 3/1995 | Slater et al. .................. 600/564 |
| 6,113,597 A | * | 9/2000 | Eggers et al. .................. 606/46 |

(Continued)

FOREIGN PATENT DOCUMENTS

| EP | 2 095 785 A1 | 9/2009 |
| JP | 2009-148575 A | 7/2009 |

(Continued)

OTHER PUBLICATIONS

Korean Intellectual Property Office, Translation of International Search Report of International Application No. PCT/US2014/048431, Mailed on Nov. 12, 2014, 2 pages.

*Primary Examiner* — Michael Peffley
*Assistant Examiner* — Daniel Fowler
(74) *Attorney, Agent, or Firm* — Brinks Gilson & Lione

(57) ABSTRACT

An electrosurgical instrument for removal of tissue from a patient and a method for doing the same. The electrosurgical instrument includes a pair of lever members each of which having an associated end effector associated. One of the end effectors includes a cutting element forming a loop on the end of the end effector. The cutting element is also configured to receive electrical energy from an electrical energy source. The other of the end effectors includes a pad that can be brought into a position generally opposing the cutting element during relative movement of the end effectors toward one another. When electrical energy is discharged from the cutting element and the end effectors moved toward one another, dissection and cauterization of tissue from a patient is facilitated.

31 Claims, 16 Drawing Sheets

(56) References Cited

U.S. PATENT DOCUMENTS

| | | |
|---|---|---|
| 6,174,309 B1 * | 1/2001 | Wrublewski et al. ............ 606/45 |
| 6,273,887 B1 * | 8/2001 | Yamauchi et al. .............. 606/48 |
| 6,293,790 B1 | 9/2001 | Hilliard |
| 7,179,254 B2 | 2/2007 | Pendekanti et al. |
| 2004/0153105 A1 | 8/2004 | Burbank et al. |
| 2005/0143726 A1 * | 6/2005 | Bortkiewicz ................... 606/41 |
| 2009/0198228 A1 | 8/2009 | Sartor |
| 2009/0254082 A1 | 10/2009 | Kornerup et al. |
| 2011/0230725 A1 | 9/2011 | Li |
| 2012/0323232 A1 | 12/2012 | Wolf et al. |
| 2013/0274740 A1 | 10/2013 | Dickson et al. |
| 2013/0274743 A1 | 10/2013 | Banfalvi |

FOREIGN PATENT DOCUMENTS

| | | |
|---|---|---|
| WO | 2007/021565 A2 | 2/2007 |
| WO | 2012/175912 A1 | 12/2012 |

* cited by examiner

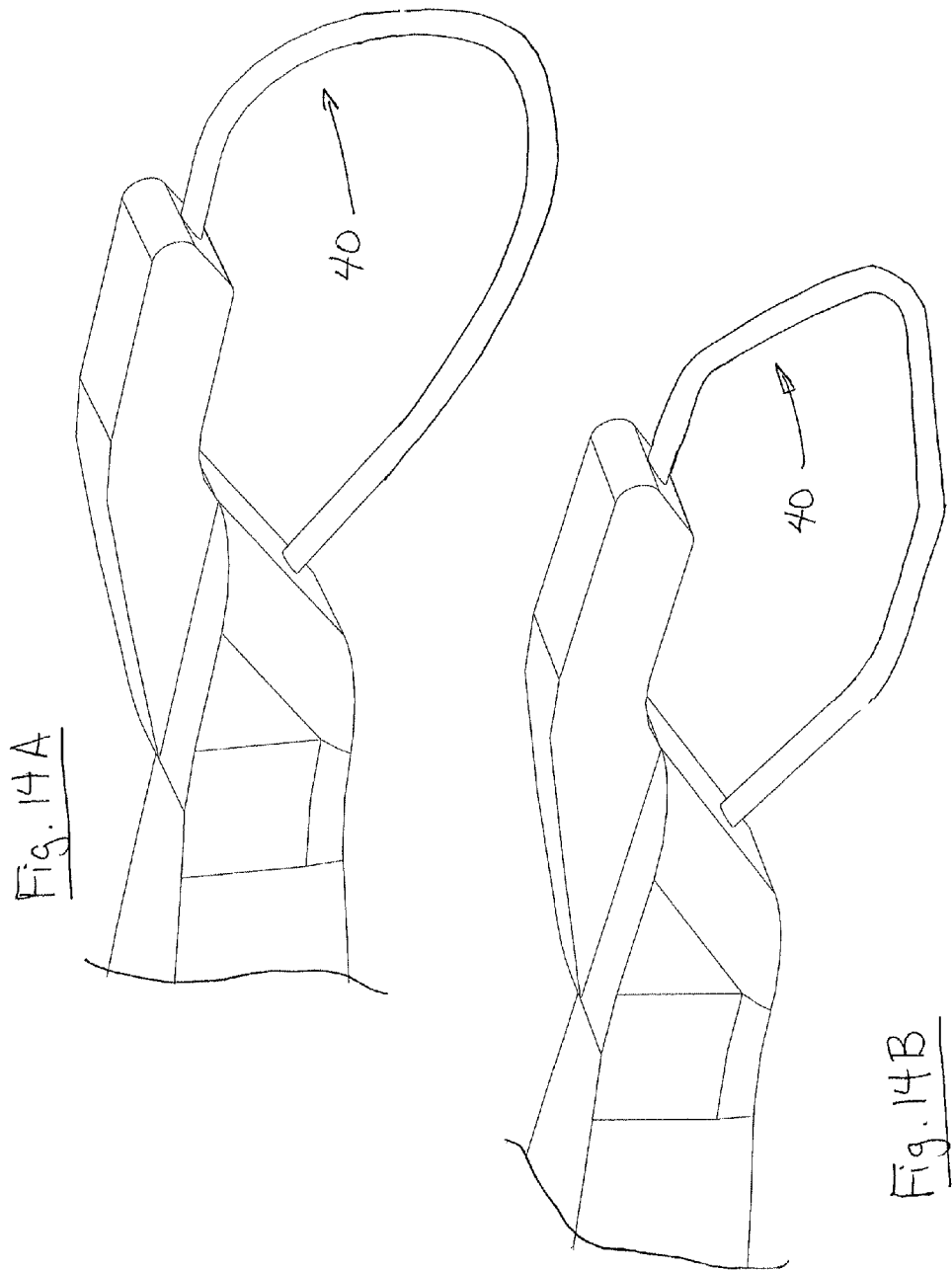

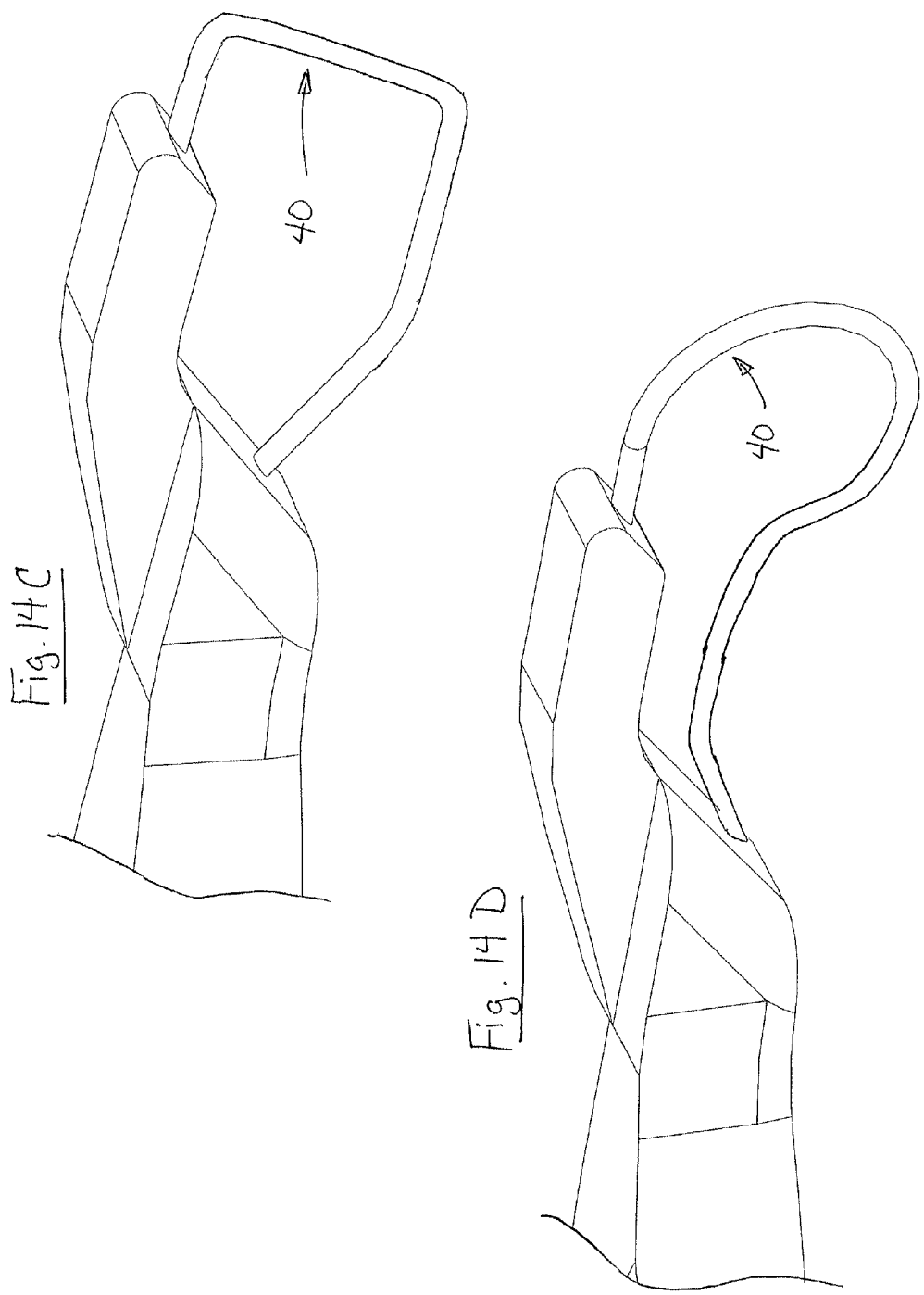

SURGICAL INSTRUMENT

CROSS REFERENCE TO RELATED APPLICATIONS

This application claims priority to U.S. Provisional Application No. 61/860,905 filed on Jul. 31, 2013, the entire contents of which is hereby incorporated by reference.

BACKGROUND OF THE INVENTION

1. Field of the Invention

The present invention generally relates to a surgical instrument for tissue removal. More specifically, the present invention relates to a surgical instrument for performing the removal of either tubal, palatine and pharyngeal types of tonsils, and even more particularly, the latter type of tonsils, which are commonly referred to as adenoids.

2. Description of Related Technology

As seen in FIG. 1, tonsils (T) and adenoids (A) are a masses of lymphoid tissue generally found in the oral and nasal cavities ($C_o$, $C_n$) respectively. The tonsils are a set of tissue located on both sides at the back of the throat. Adenoids, on the other hand, comprise a clump of tissue, not directly visible from outside the mouth, located rearward of the nasal cavity and above the soft palate, generally where the nasal cavity merges with the throat. Tubal tonsils are also present in the pharyngeal cavity, but are not illustrated.

Both tonsils and adenoids are subject to infection, particularly in children. When infected, the enlarged tissue may impair breathing through the nose, cause snoring, cause retention of fluid (and, therefore, infection of the ears (caused by the adenoids)), cause accumulation of nasal secretions (and, therefore, sinus infections (caused by the adenoids), and cause difficulty in swallowing and breathing (caused by the tonsils). Since tonsil tissue has been observed to serve an immunological or other function in adulthood, when infections are common and recurring, one preferred treatment is the surgical removal of the tissue, which is called either an adenoidectomy or a tonsillectomy.

Common methods for removing the adenoids and tonsils include utilization of a curette, forceps or an electrocautery device. A curette is a surgical instrument having a spoon or otherwise shaped end that is used to scrape and remove the desired tissue. With an electrocautery device, radio-frequency energy is applied to tissue, heating the water in the local tissues, thereby weakening the tissue, allowing mechanical scraping removal and cauterizing of removal site to reduce or stop bleeding.

Of the two procedures, some physicians prefer electrocautery since it minimizes the bleeding associated with removal of the tissue. However, current instruments for electrocautery are not specifically designed for rapid removal of either the tonsils or the adenoids.

SUMMARY

In a general aspect, the invention provides an electrosurgical instrument for removal of tissue from a patient.

In another aspect, the invention provides an electrosurgical instrument comprising: a pair of lever members; an end effector associated each of the lever members for the removal of tissue, the end effectors being supported by the lever members for relative movement generally toward one another; one of the end effectors including a cutting element that is configured to receive electrical energy from an electrical energy source, the cutting element forming a loop on the end of the end effector; the other of the end effectors including a pad provided thereon, the cutting element and the pad being brought into a position opposing one another during relative movement of the end effectors toward one another; and wherein electrical energy is discharged from the cutting element facilitating dissection and cauterization of the tissue of the patient.

In a further aspect of the invention, the cutting element is a wire.

In another aspect of the invention, the loop defines an opening therein.

In an additional aspect of the invention, the pad corresponds in shape to the loop.

In another aspect of the invention, the pad has an overall size that is smaller than the opening.

In still another aspect of the invention, the cutting element and pad are moveable between open and closed positions, in the closed position at least a portion of the pad extends through a plane defined by the cutting element.

In yet another aspect of the invention, the cutting element defines a plurality of radii of curvature.

In a further aspect of the invention, the loop is a closed loop.

In an additional aspect of the invention, the loop is formed at least in part by the cutting element.

In still a further aspect of the invention, the pad is directly opposed to the loop.

In another aspect of the invention, the pad includes a leading surface, in a closed position of the electrosurgical instrument, the leading surface being located on one side of a plane defined by the cutting element and, in an open position of the electrosurgical instrument, the leading surface being located on an opposing side of the plane defined by the cutting element.

In an additional aspect of the invention, the loop is an interrupted loop.

In yet another aspect of the invention, the end effector having the cutting element includes a base and a riser extending off of the base.

In a further aspect of the invention, the riser is laterally offset from the base.

In still another aspect of the invention, the loop extends into the riser.

In an additional aspect of the invention, the riser defines a portion of the loop.

In another aspect of the invention, the cutting element is configured to produce a power density of between 0.2 and 17.1 $W/mm^2$.

In an additional aspect of the invention, the cutting element has a diameter and a length configured to achieve a power density of between 0.2 and 17.1 $W/mm^2$ in conjunction with a power supply.

In further aspect of the invention, the cutting element has a diameter and a length achieving a power density of between 0.2 and 17.1 $W/mm^2$ in conjunction with a power supply providing a frequency in the range of 100 KHz to 5 MHz (intermittent or continuous).

In another aspect of the invention, the electrosurgical instrument is coupled to a power supply and the power supply can account for impedance variations (for example by: impedance matching, voltage adjustment, and/or current adjustment) with the electrosurgical instrument and tissue to be removed thereby.

In an additional aspect of the invention, the pad is not directly opposed to the loop.

In a further aspect of the invention, the loop extends in a direction transverse to the direction of relative movement of the end effectors toward one another.

In still another aspect of the invention, the loop is oriented in a plane transverse to the direction of relative movement of the end effectors toward one another.

In another aspect of the invention, a method of dissecting tissue from a patient utilizing an electrosurgical instrument is provided, the method comprising: providing an electrosurgical instrument having a pair of lever members with an end effector associated with each of the lever members and supported by the lever members for relative movement in a direction toward one another, one of the end effectors including a cutting element that is configured to receive electrical energy from an electrical energy source, the cutting element forming a loop having a central opening on the end of the end effector; positioning the loop on one lateral side of the tissue to be removed and positioning the other of the end effectors on an opposing lateral side of the tissue to be removed; causing relative movement of the end effectors toward each other; providing electrosurgical energy to the cutting portion and discharging the electrosurgical energy through the cutting element to the tissue to be removed; dissecting and cauterizing the tissue; passing the dissected tissue through the opening of the loop; and removing the dissected tissue from the patient.

In a further aspect of the invention, the cutting element and at least part of the loop is formed by a length of wire, the electrosurgical energy being discharged through the length of wire.

In still a further aspect of the invention, the step of positioning the loop on one lateral side of the tissue to be removed includes performing blunt dissection to position the loop between adjacent portions of tissue.

In another aspect of the invention, the step of causing relative movement of the end effectors toward each other causes part of the other of the end effectors to at least partially extend though the opening of the loop.

In an additional aspect of the invention, the step of causing relative movement of the end effectors toward each other causes a leading face of the other of the end effectors to pass completely though the opening of the loop.

In yet another aspect of the invention, the step of passing the dissected tissue through the opening of the loop at least partially passes the dissected tissue through the loop.

In a further aspect of the invention, the step of passing the dissected tissue through the opening of the loop completely passes the dissected tissue through the loop.

In another aspect, the tissue is tonsil tissue and more particularly pharyngeal tonsil tissue.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIGS. 14A-14E are diagrammatic illustrations of alternative configurations for the cutting element of the cautery forceps.

DETAILED DESCRIPTION

The present invention provides an electrosurgical instrument for removal of tissue. While those skilled in the art will appreciate that electrosurgical instruments incorporating the principles of the present invention are suitable for use in removing multiple types of tissue, as described herein the instruments are utilized for removal of tonsil tissue, such as but not limited to the palatine tonsils (commonly referred to as just the "tonsils"), tubal tonsils and the pharyngeal tonsils (commonly referred to as the "adenoids"). For simplicity, the discussion that follows utilizes reference to adenoids or adenoid tissue. It is to be understood that, throughout this written description, the use of the terms adenoid(s) or adenoid tissue is intended to be generic for all types of tonsil tissue, unless specifically otherwise noted, and that the invention is applicable to all of the above types of tonsils.

Overview

Figure 1:
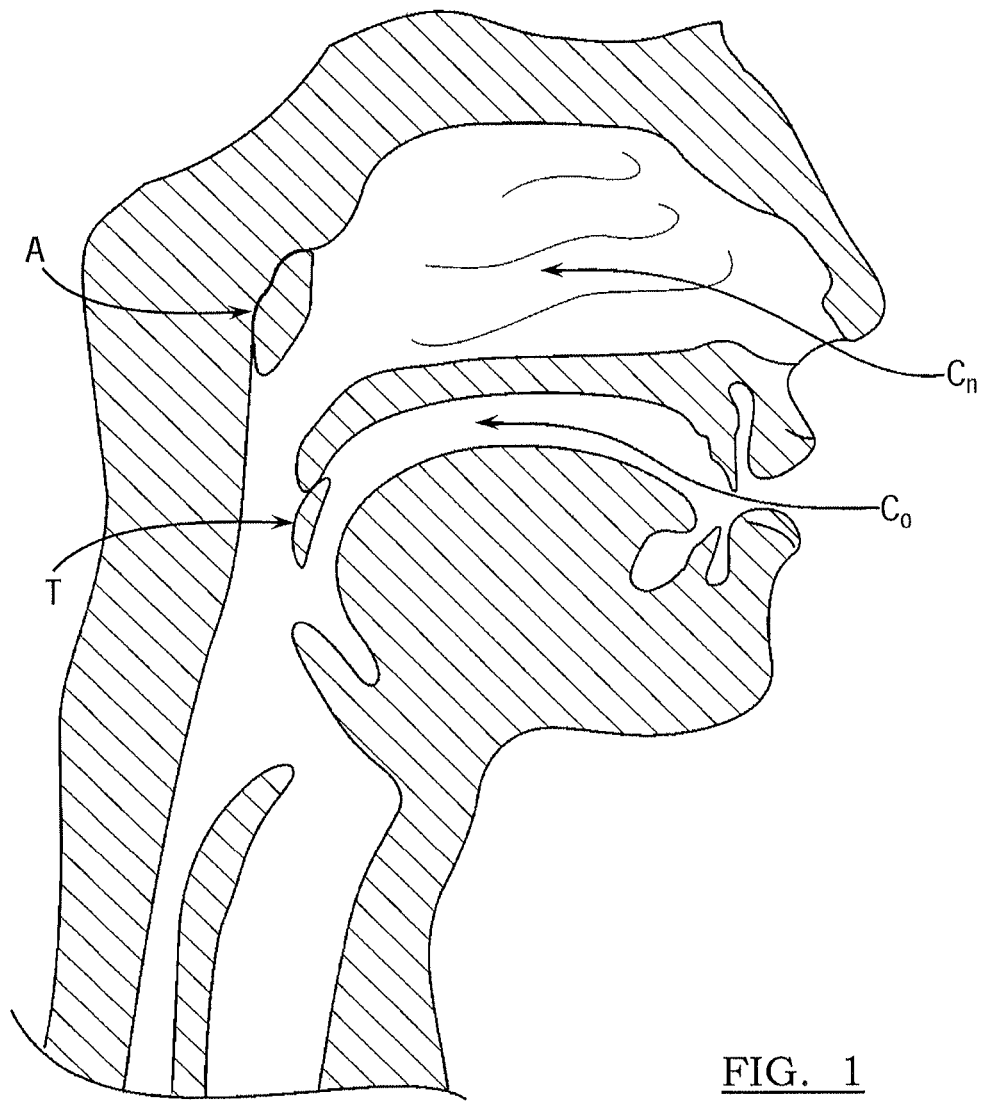
FIG. 1 is a diagrammatic illustration of the oral and nasal cavities of a person showing the relative locations of the tonsils and adenoids therein.
Figure 2:
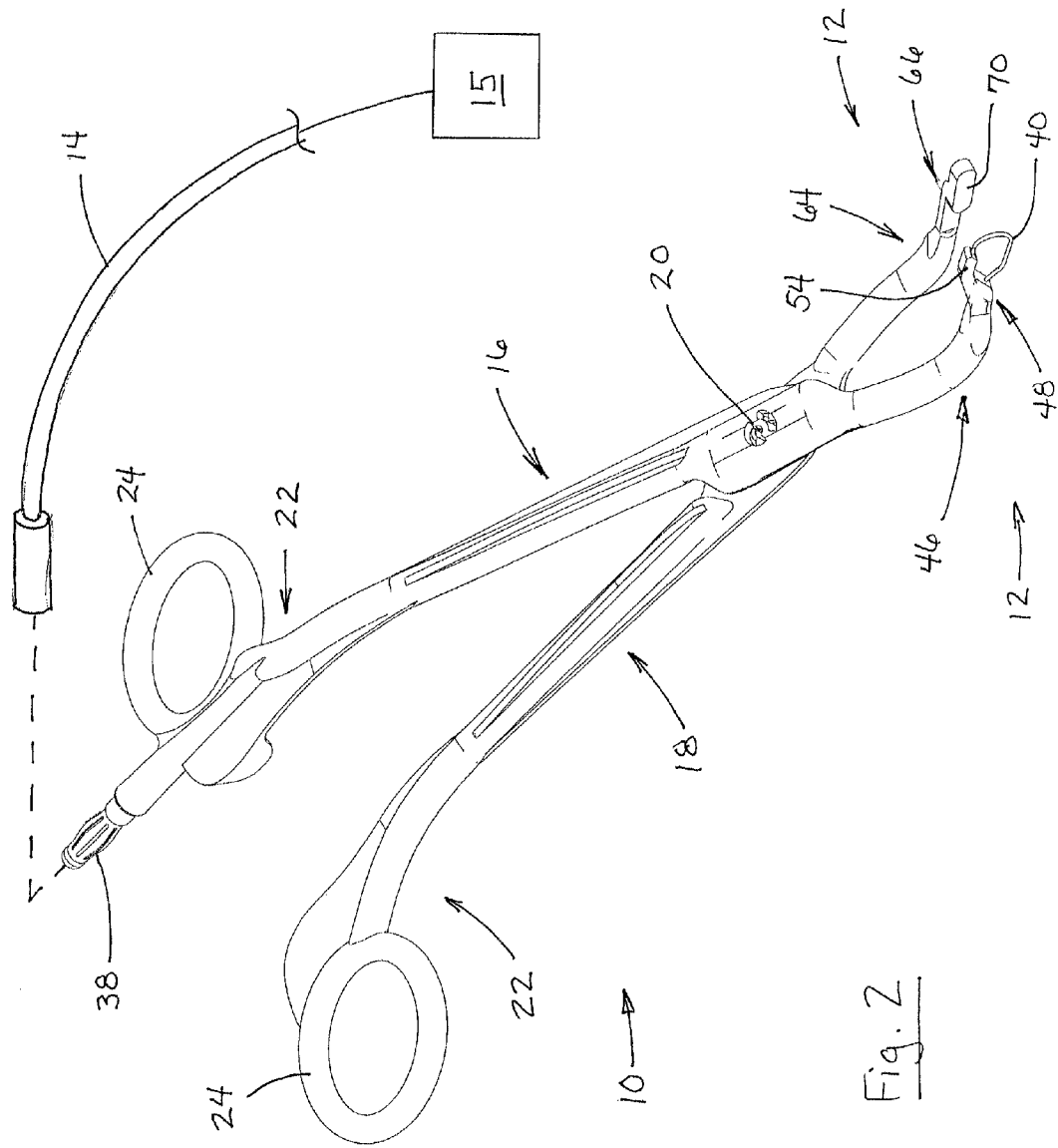
FIG. 2 is a perspective view of cautery forceps embodying the principles of the present invention.
Figure 3:
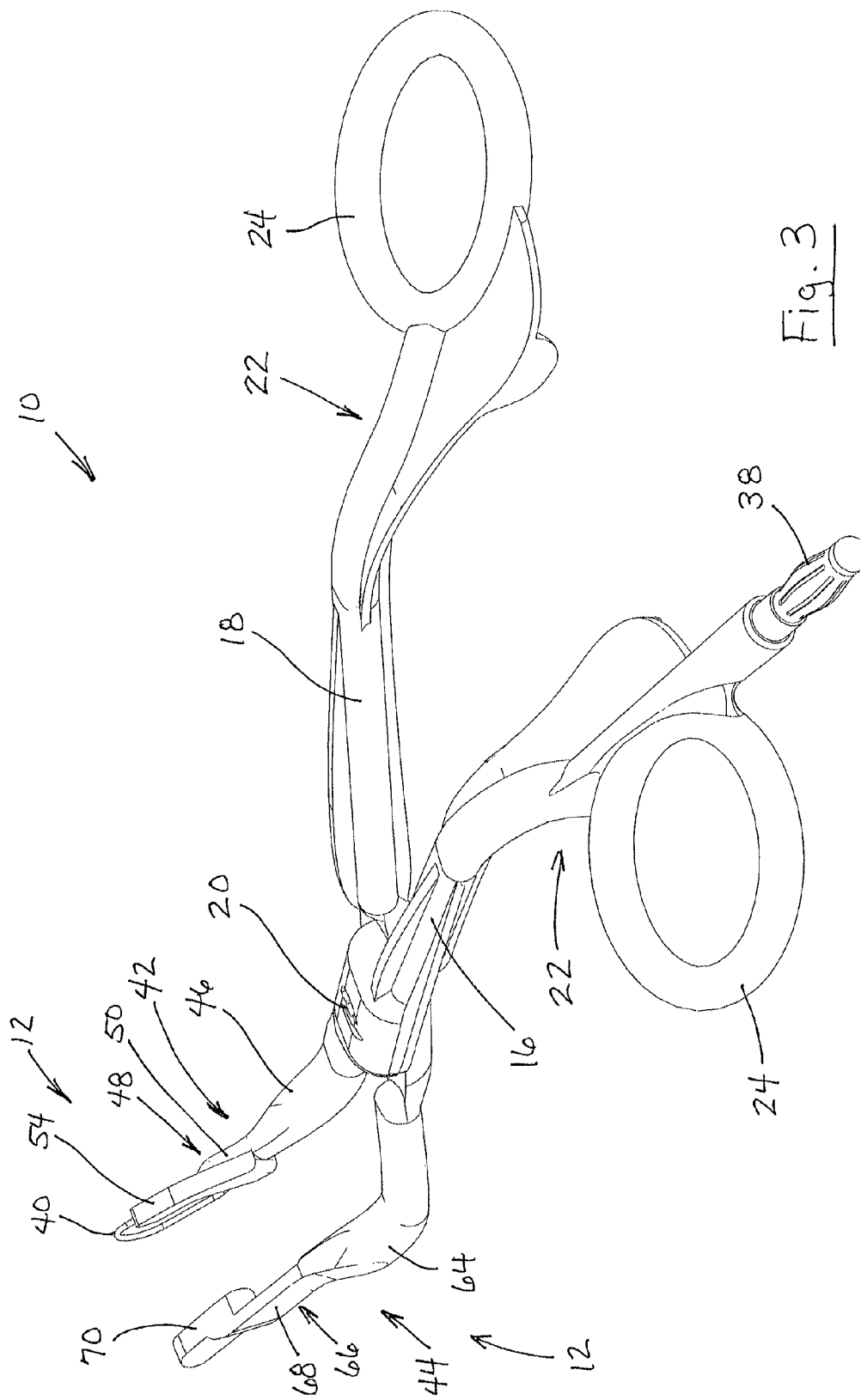
FIG. 3 is another perspective view of cautery forceps embodying the principles of the present invention.
Figure 4:
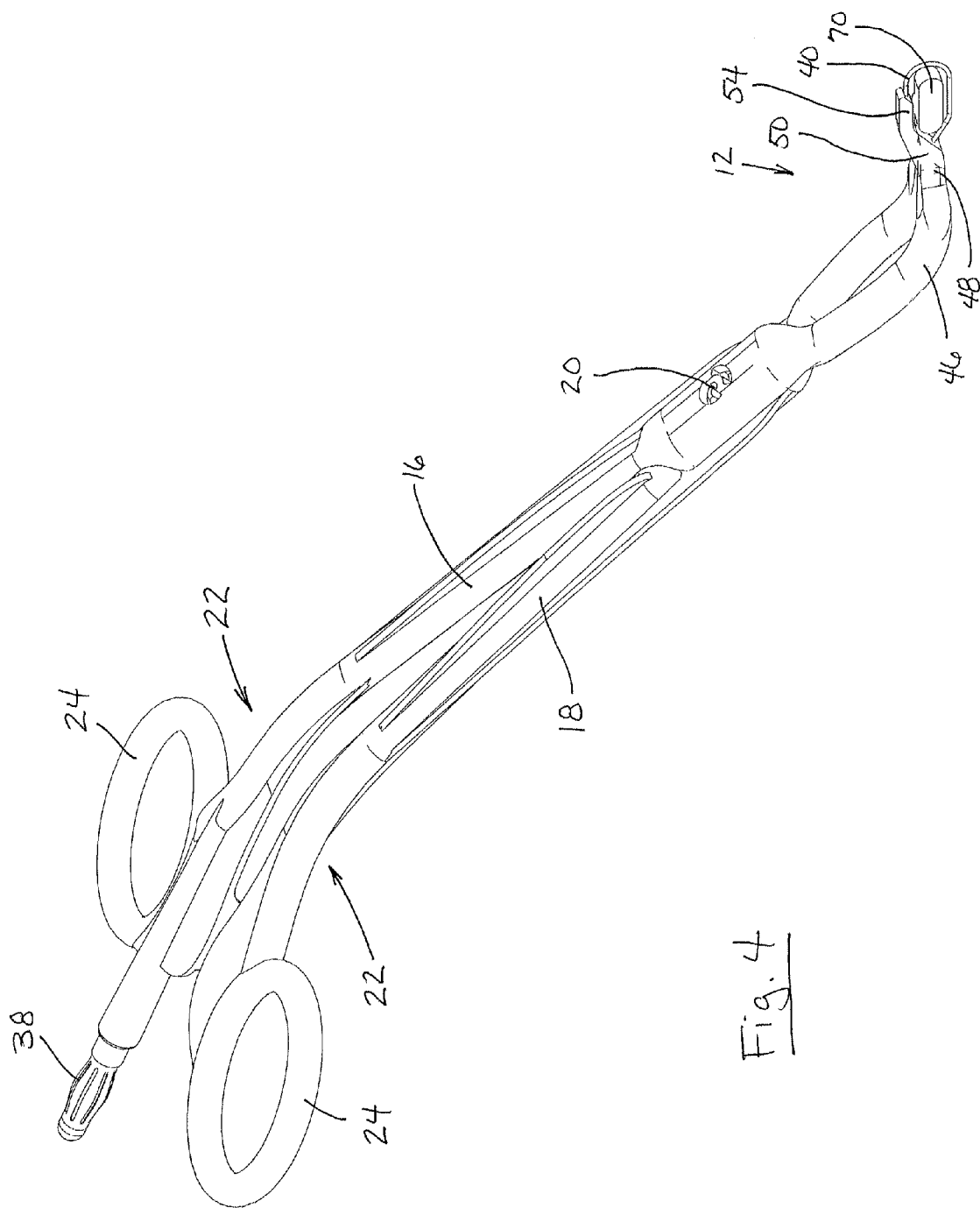
FIG. 4 is a perspective view of cautery forceps, similar to the view of FIG. 2, with the end effectors in the closed position.
Figure 5:
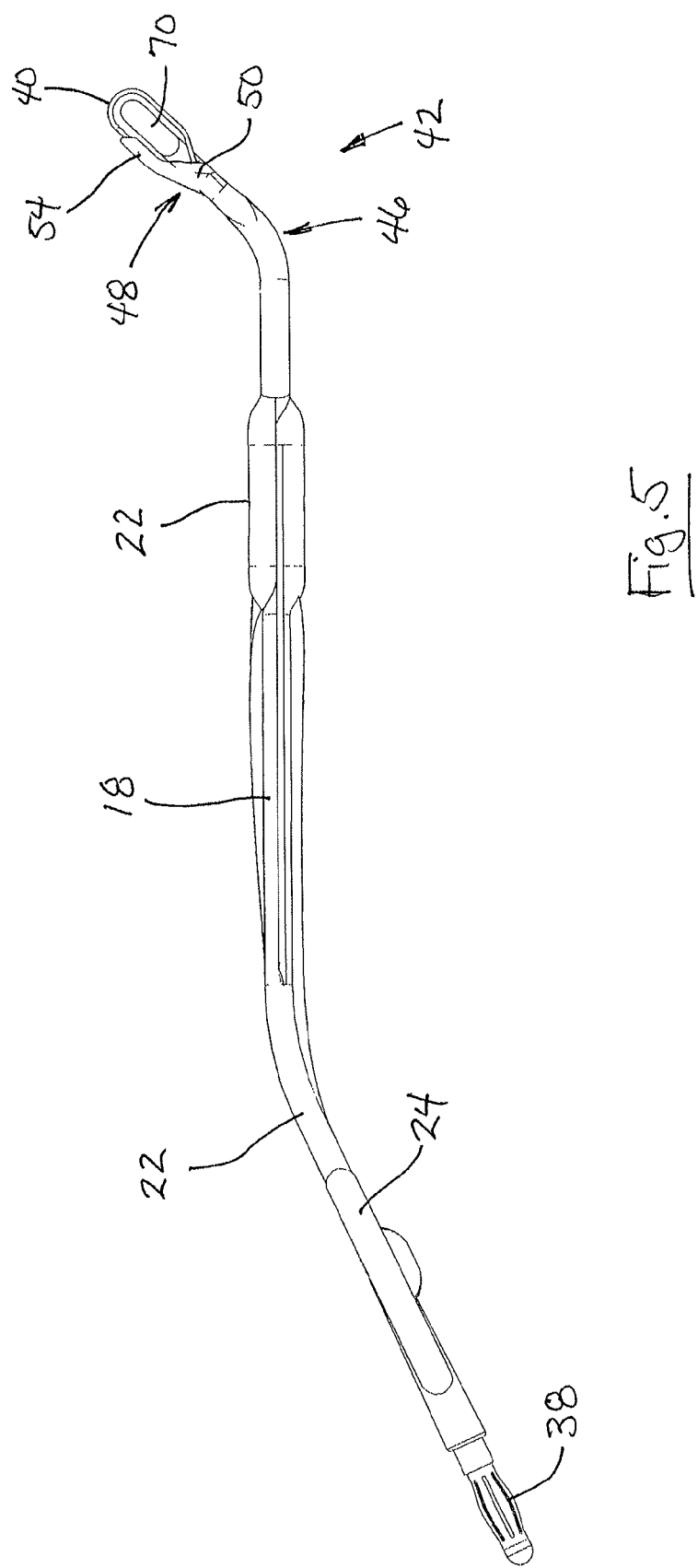
FIG. 5 is a side view of cautery forceps seen in FIG. 4.

Referring now to FIGS. 2 and 3, illustrated therein and designated at 10 is an electrosurgical instrument in accordance with the principles of the present invention. As seen in these figures, the electrosurgical instrument 10 is generally in the shape of forceps. Unlike common forceps, however, the electrosurgical instrument 10, which is hereinafter referred to as cautery forceps 10, includes a pair of end effectors 12, one of which has an exposed cutting element (further discussed in detail below). Additionally, the cautery forceps 10 include a means 14, such as a power cable, by which the cutting element is to be connected to a suitable electrical power source.

During use, the end effectors 12 are spread apart and positioned such that adenoid tissue to be excised is located between the end effectors 12. Once positioned, electrical current is supplied to the cautery forceps 10 and, more particularly, the cutting element. While the cautery forceps 10 are being energized, the end effectors 12 are brought toward one another and to bear against the adenoid tissue that is to be excised. Electrical current will flow from the cutting element, to the adenoid tissue, and out of the patient's body at another electrode, which has been attached in a remote location apart from the adenoid tissue. With this discharging of current, radio-frequency energy is locally applied to tissue, heating the water in that tissue. The heating of the water within the tissue results in a weakening and/or severing of the tissue, allowing for the dissection of the tissue and the simultaneous cauterizing of dissection site.

Power Source

The power source may be one of a variety of sources. Preferably, the power source 15 is an available source of power located in the room where the cautery forceps 10 are to be used. As such, the power source 15 includes the componentry required to provide the proper voltage, current and frequency for electrocautery surgery. Generally, electrocautery requires a frequency in the radio frequency range, above 100 KHz and up to 5 MHz. This power source 15 can be provided as an integrated system, such that the power cable 14 is merely plugged into an outlet (not show) in the room. Alternately, the power source 15 can be provided as a stand-alone power system located in the room or as a battery based system.

While many tissues may be excised via the cautery forceps 10 with a wide variety of power sources, some power sources are not as effective with other types of tissues. It has been found that certain tissues are high impedance tissues and that the cutting of these tissues may not be as effective with general and, sometimes older, power sources. It has been further found that these higher impedance tissues, which include adenoid tissue, require power supply which can account for impedance variations (for example by: impedance matching, voltage adjustment, and/or current adjustment).

Construction

The cautery forceps 10 according to the present invention are monopolar in their construction. In such a construction, the cautery forceps 10 themselves include a single electrode, the cutting element, in one of the end effectors 12, which is further discussed below. During use, current flows from the electrode, through or about the patient, to a return electrode affixed elsewhere on the patient's body.

In an alternative embodiment, the cautery forceps 10 may be of a bipolar construction. In a bipolar construction, a second electrode is also provided on the other end effector 12 and electrical current passes primarily from the electrode on one end effector to the electrode on the other end effector. The current thus passes primarily by way of a localized portion of tissue, namely the tissue located between the electrodes. This is in contrast to current generally flowing via the body of the patient to the remotely located electrode used in a monopolar construction. By facilitating the flow of electric current more generally by way of the body, the monopolar construction, when compared to a bipolar construction, is believed to have less chance of "tissue bridging" at the end of the cut. Tissue bridging is the situation where previously moist tissue between two electrodes hardens before being severed. As a result, no further electrical current passes by way of the tissue from one end effector to the other and no further dissection can be made.

The cautery forceps 10 of the illustrated embodiment generally comprise two lever members 16, 18, that are pivotably connected together at a pivot 20 and are arranged such that the cautery forceps 10 operate in a traditional, scissors-like manner. In such a construction, the lever members 16, 18 cross one another at the pivot 20. Each lever member 16, 18 includes a handle 22 at one end and the end effector 12 at the other end. The handles 22 may be formed in a variety of configurations, including finger rings or grips 24, as readily seen in FIGS. 2 and 3. With this construction, by bringing the handles 22 (or the finger rings 24) together, the end effectors 12 are likewise moved in a direction toward one another.

The lever members 24, 26 may be of a monolithic construction, but are preferably constructed with a subframe 26 formed of a polymer resin, or other material, such as polycarbonate, polyetheretherketone (PEEK), acrylonitrile butadiene styrene (ABS), high-density polyethylene (HDPE), acrylic, and polyacrylamide (PARA), and preferably a 30-70% glass filed resin. The subframe 26 is overmolded with a polymer resin or other material, such as a material from the above listing, to define the exterior surface of the cautery forceps 10. While overmolded with the polymer resin, the subframes 26 need not be entirely overmolded, and the subframes 26 themselves may define part of the exterior surface of the cautery forceps 10. Preferably, the material defining the exterior surface of the cautery forceps 10, at least in the regions of the finger rings 24 of the handles 22, forms a surface that facilitates grasping and limits potential slipping of the cautery forceps 10 in the hands of the user.

Figure 6:
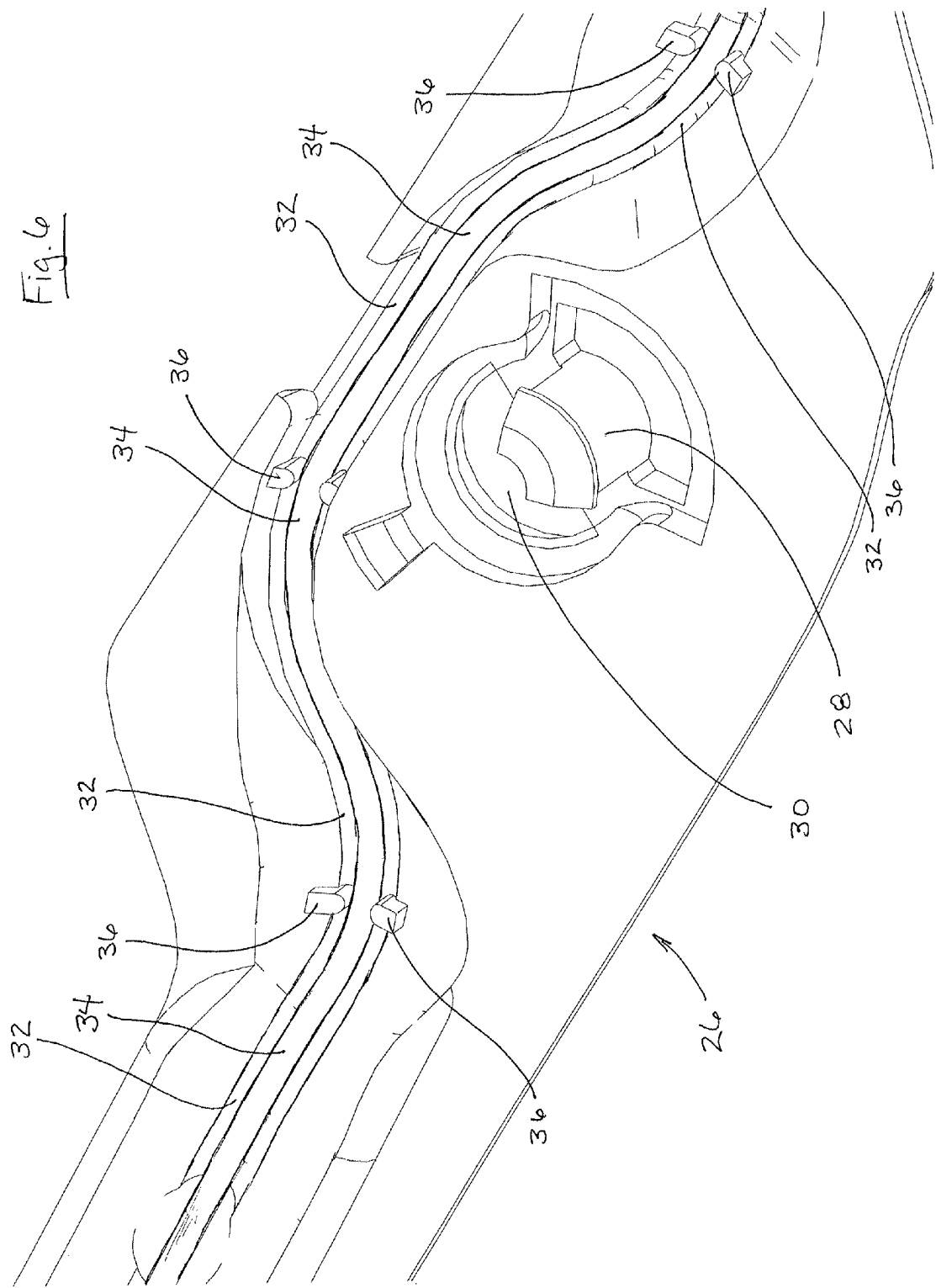
FIG. 6 is an enlarged perspective illustration of a portion of the cautery forceps during one stage of manufacture.
Figure 7:
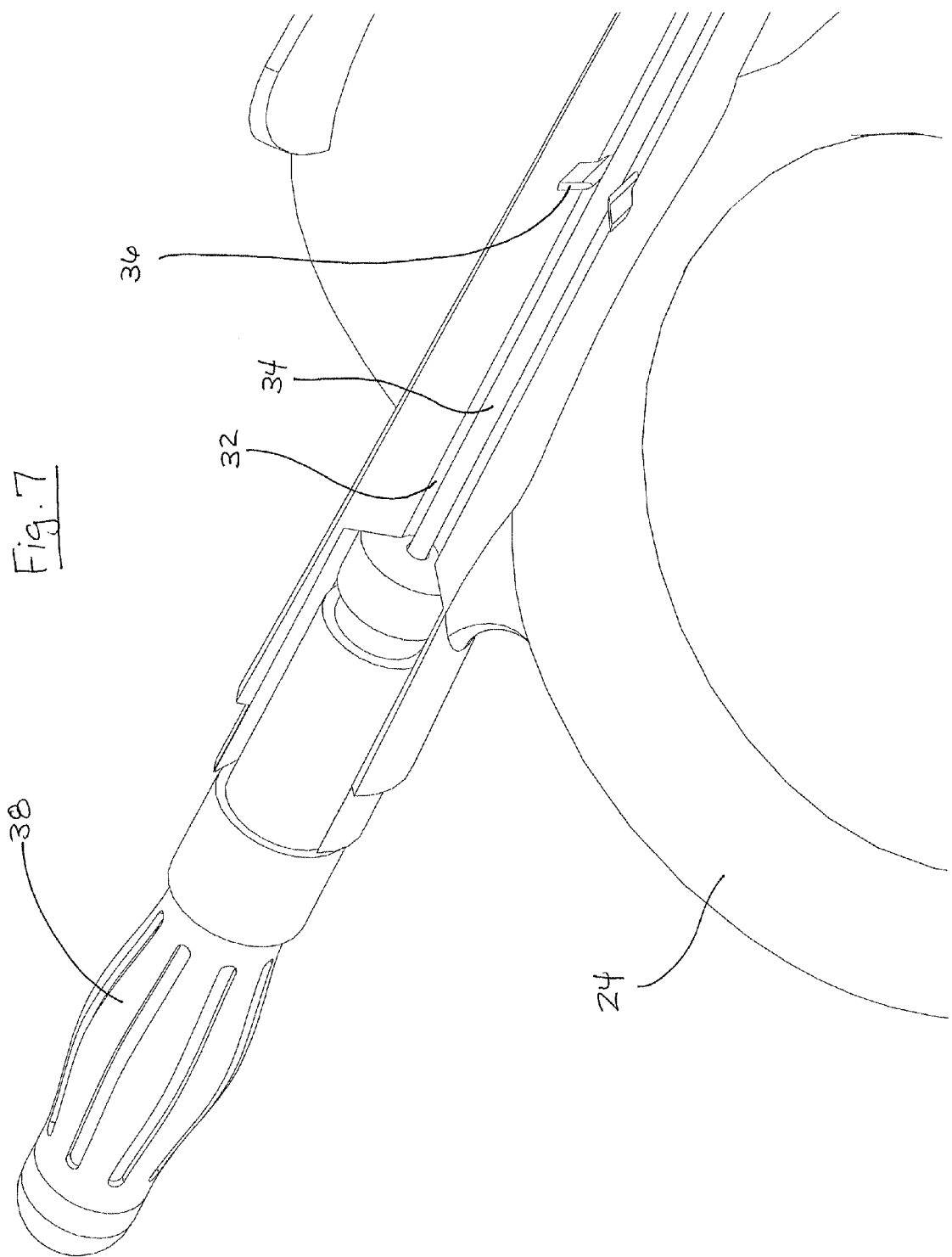
FIG. 7 is an enlarged perspective illustration of another portion of the cautery forceps during one stage of manufacture.
Figure 8:
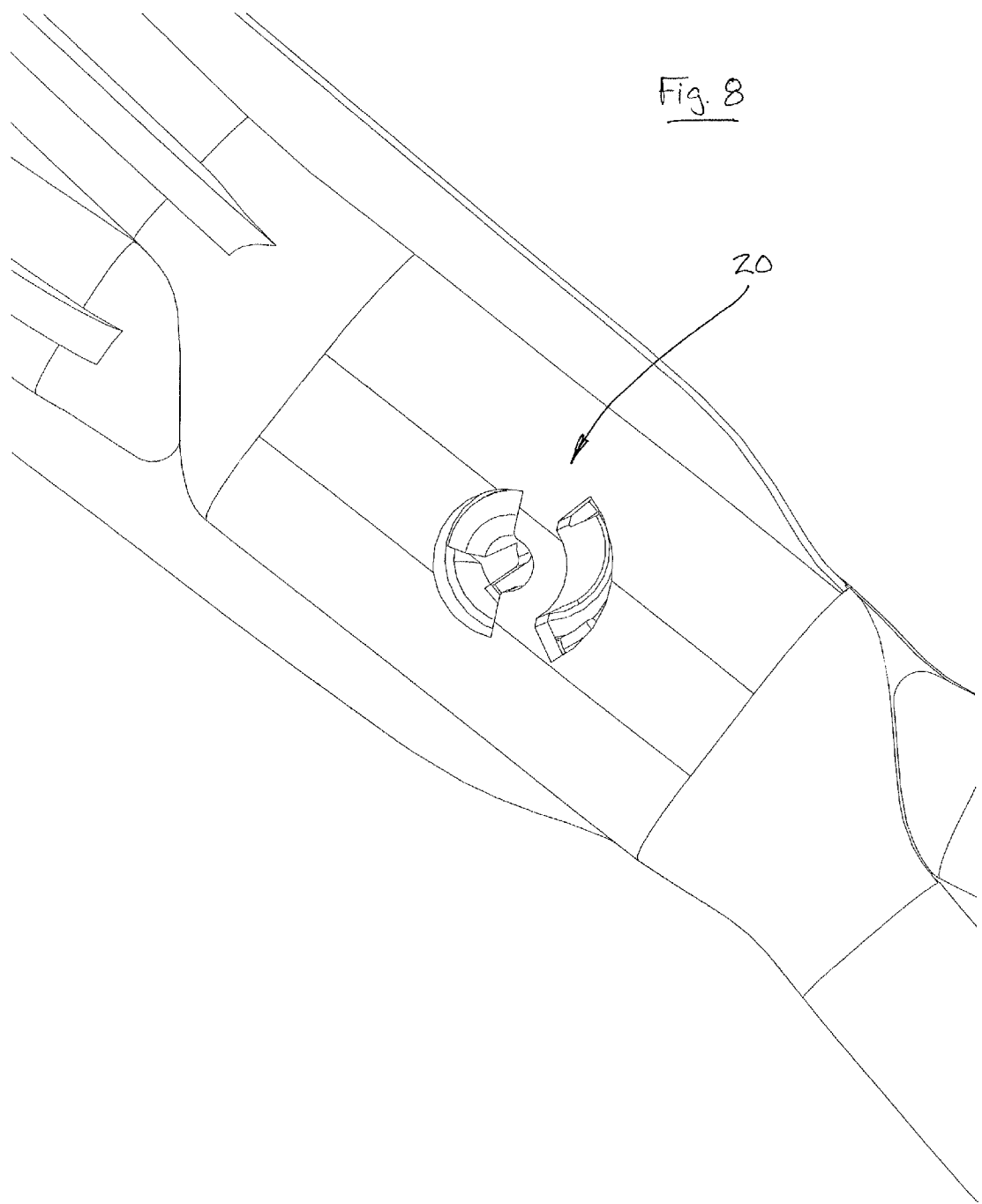
FIG. 8 is an enlarged perspective illustration of still another portion of the cautery forceps during one stage of manufacture.

One or both of the subframes 26 may include a boss 28 defined by one or more snap tabs, as shown in FIG. 6. The other of the subframes 26 includes a bore 30 into which the corresponding snap tab 28 is received and retained. The boss 28 and bore 30 thus cooperate to define the pivot 20 of the cautery forceps 10. The pivot 20, however, may be defined through other constructions, such as but not limited to the inclusion of a pivot axle and/or retention screw.

In the illustrated construction, one of the subframes 26 further includes portions defining a raceway 32. The raceway 32 is sized to receive a wire or other conductor 34 for the passage of electrical current through the lever member 16 to the cutting element of the corresponding end effector 12. If the subframe 26 is overmolded with a non-conductive material, the wire 34 may not need to be insulated when positioned within the raceway 32, but may be insulated if desired. To retain the wire 34 within the raceway 32, opposed retainers 36 are provided at spaced intervals along the raceway 32. Preferably, the retainers 36 define a distance between them that is less than the nominal diameter of the wire 34 and, therefore, frictionally engage and retain the wire 34.

At the proximal end of this lever member 16, the wire 34 is attached (soldered, crimped or otherwise connected) to an electrical connector 38, such as banana connector (plug or socket). As seen in FIG. 3, the electrical connector 38 is configured as a banana plug. The electrical connector 38 in turn connects to the power cable 14 mentioned above. At the distal end of this lever member 16, the wire 34 is attached (soldered, crimped or otherwise connected) to the cutting element, designated at 40.

As thus far described, the end effectors 12 have been collectively referenced and designated at 12. The construction and function of each of the end effectors 12, however, is different. Accordingly, when discussing the end effectors 12 in detail, the end effectors 12 will be referenced and designated individually as a cutting end effector 42 and a resisting end effector 44. As implied by the above naming convention, the cutting element 40 is provided in the cutting end effector 42.

The cutting end effector 42 extends from the distal end of the lever member 16 and includes a curved arm 46 at the end of which is a tip portion 48. The curvature of the arm 46 is such that the arms 46 curve at least in a direction transverse to the relative movement of the lever members 16. This curvature, however, need not be planar in nature. Rather, the curvature may exhibit a three dimensional curvature.

The tip portion 48 includes the cutting element 40, which extends from a base 50 and preferably forms a loop. In forming the loop, an end 52 of the cutting element 40 is generally returnly bend and extends back into a riser or protuberance 54 formed off of the base 50. The protuberance 54 may therefore be seen as forming a portion of the loop in conjunction with the cutting element 40. It should be noted that the cutting element 40 need not, but may, extend back through the protuberance 54 to a point where it contacts itself, thereby forming a closed loop with itself. Rather, the cutting element 40 may terminate at a point within the protuberance 54 or base 50, without contacting itself, forming a closed loop only in the sense that it does so in conjunction with the protuberance 54. In another embodiment, the cutting element 40 may terminate prior to the protuberance 54 or base 50, such that the end 52 of the loop is freely suspended and the resulting loop is not a completely closed loop, but rather an interrupted loop. Therefore, the term loop, as used herein, may encompass both a closed loop and an interrupted loop, unless one interpretation is specifically required by the context of usage.

The orientation of the loop formed by the cutting element 40 is such that it facilities insertion of the loop between individual bands of adenoid tissue. The loop therefore generally defines a plane oriented in a direction that is also transverse to the relative movement of the lever members 16.

The shape of the loop formed by of the cutting element 40 may be one of a variety of shapes. Preferably, the shape includes one or more bends such that various sections of the cutting element 40 can be used to effectuate different types of cuts and depths during removal of the adenoid tissue. At least a portion of the loop defined by the cutting element 40, however, should exhibit a radius of curvature that is less than the curvature defined by the surface of the adenoid tissue. While the curvature of the surface of the adenoid tissue will vary from patient to patient, the inventors' have found that providing a radius of curvature of about 3 mm, over a portion of the cutting element 40, will be sufficient for a substantial majority of patients.

Figure 10:
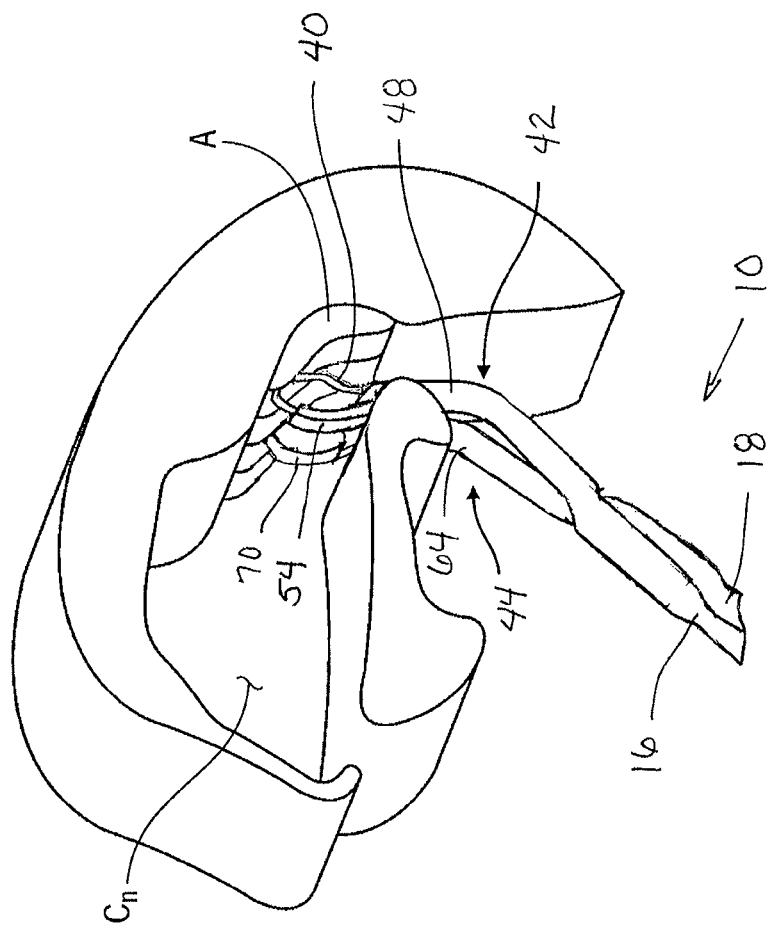
FIG. 10 is a diagrammatic illustration of the cautery forceps positioned at the interface of the oral and nasal cavities and adjacent to the soft palate and adenoids, as may be positioned at the initiation of use.
Figure 11:
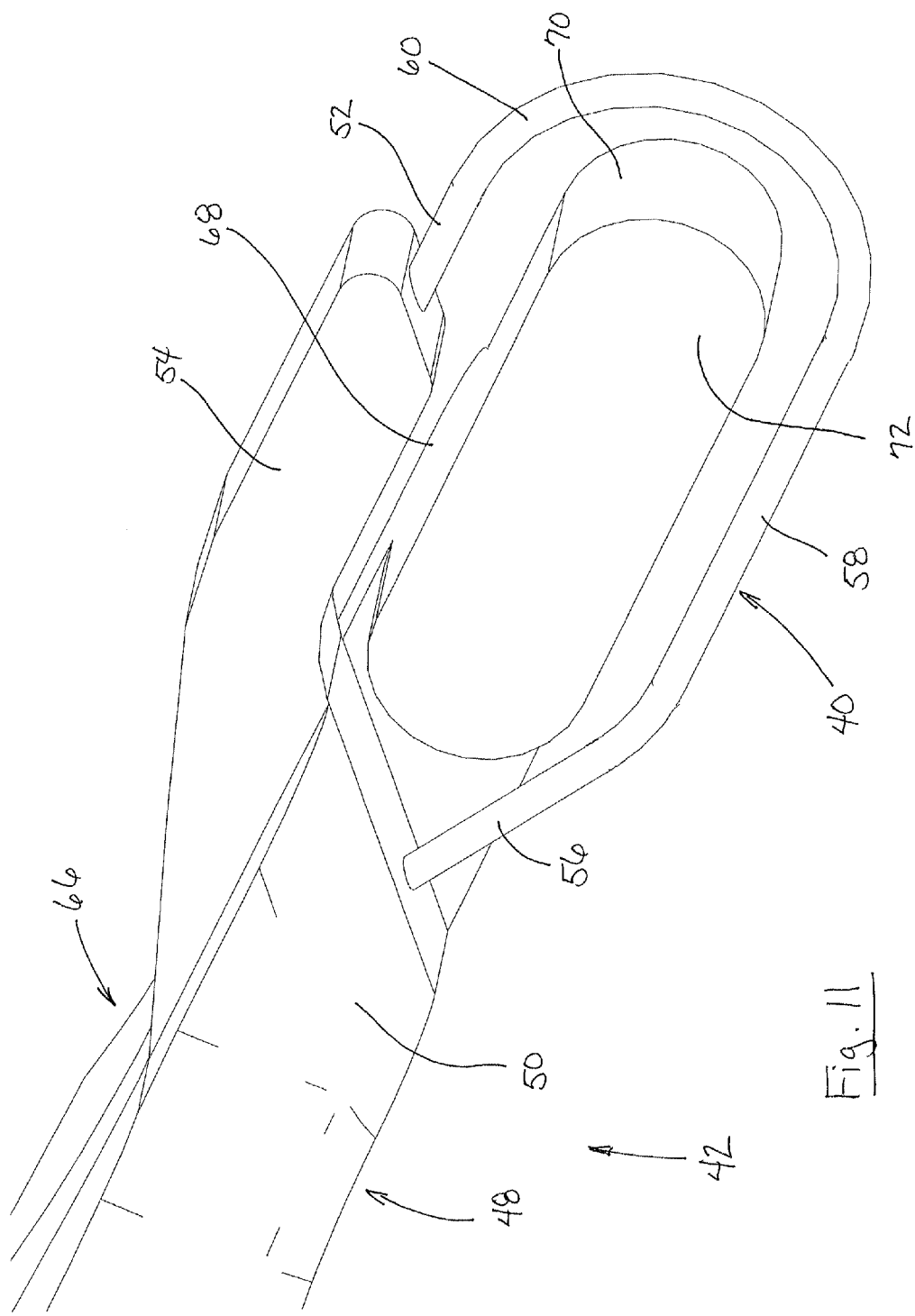
FIG. 11 is an enlarged perspective view of the end effectors of the cautery forceps of FIG. 9 in the closed position.
Figure 12:
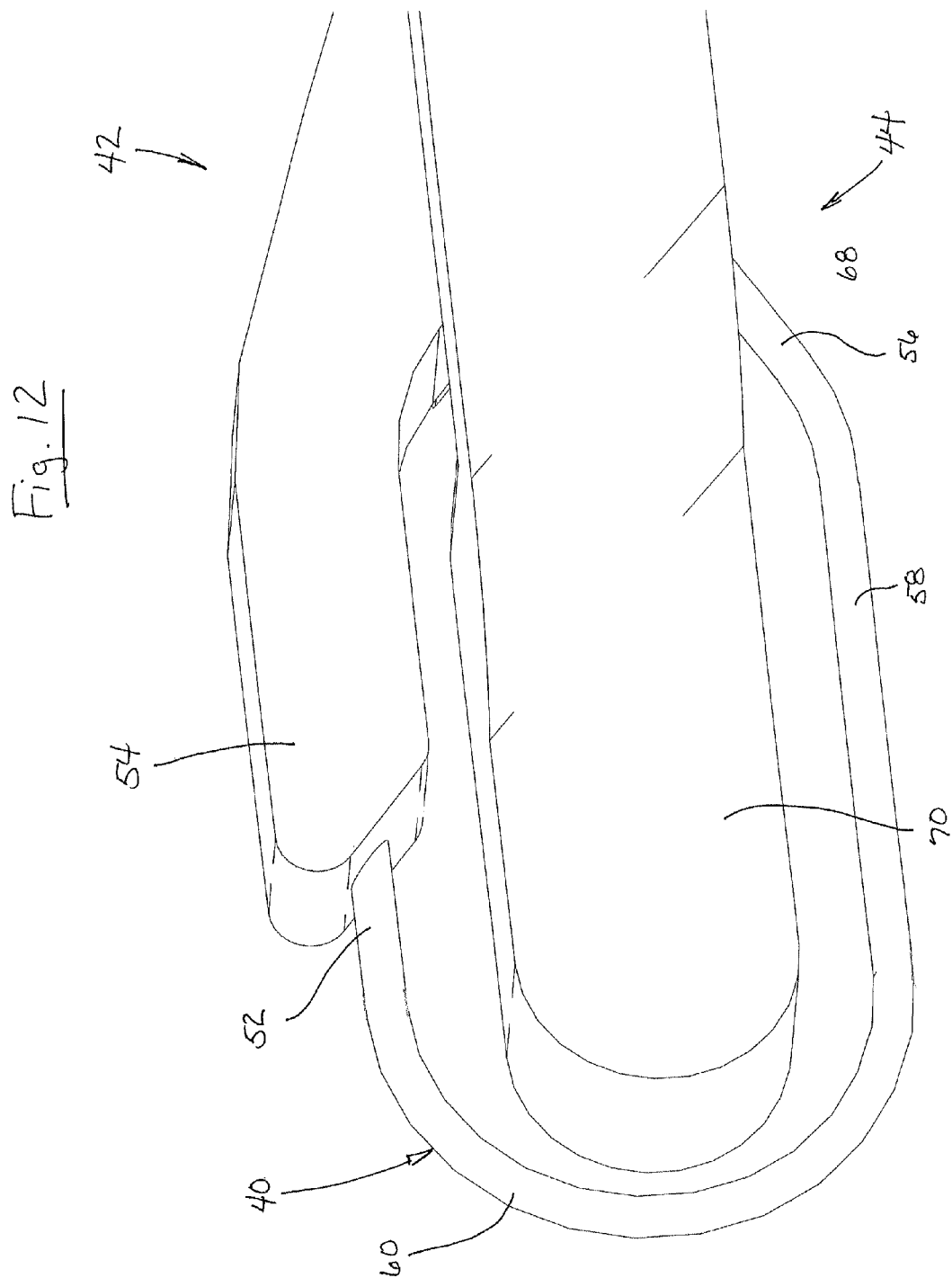
FIG. 12 is an enlarged perspective view of the end effectors in the closed position and viewed from the opposite side from FIG. 11.
Figure 13:
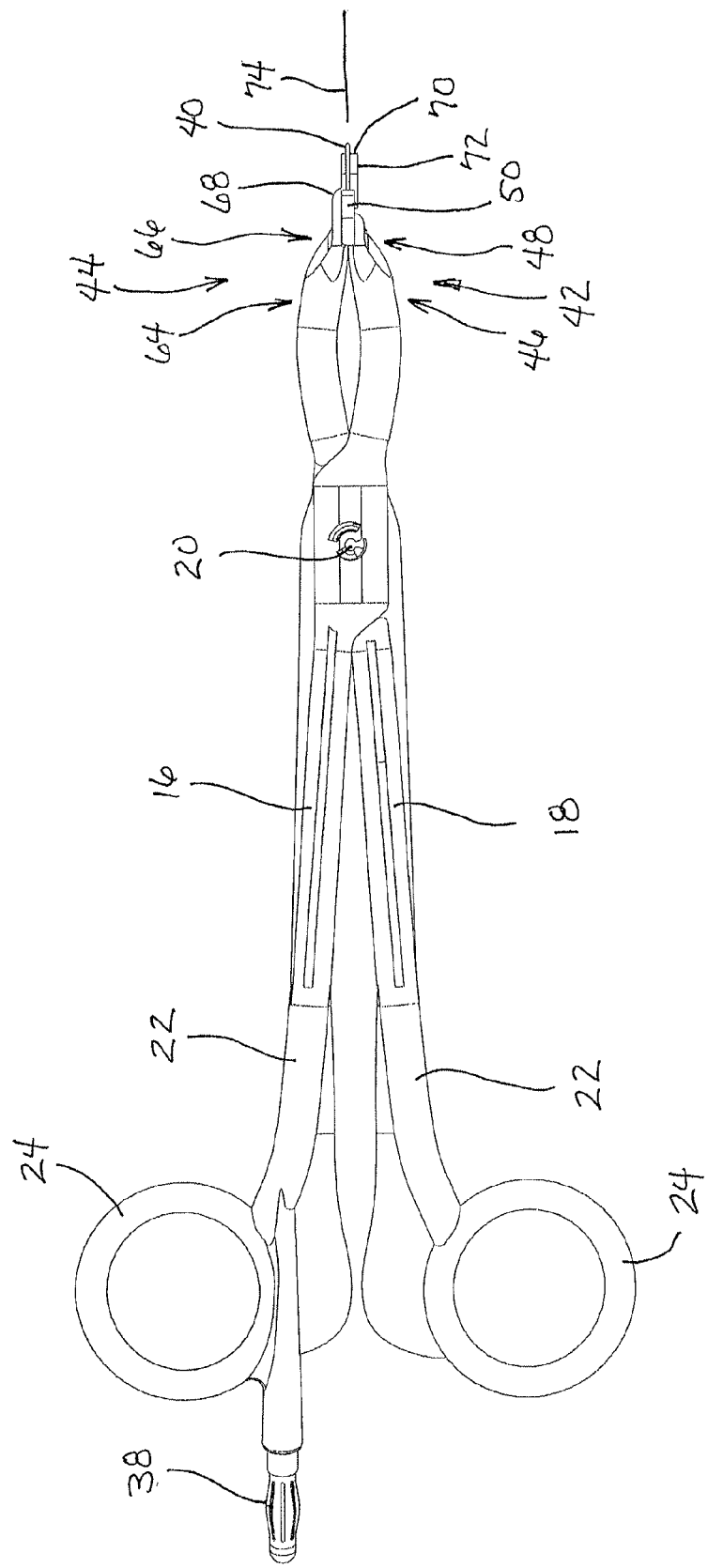
FIG. 13 is a top plan view of the cautery forceps in the closed position.
Figure 14E:
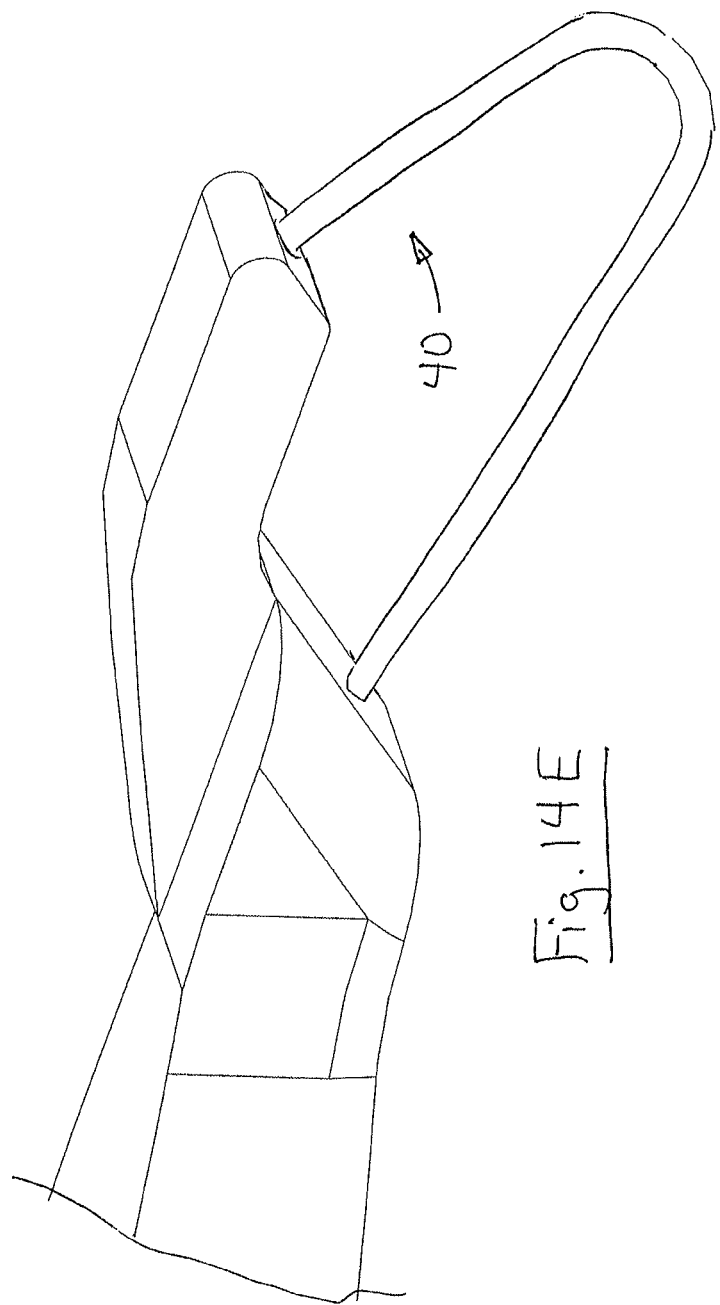

Not providing the cutting element 40 with a sufficient radius of curvature will result in the cutting element 40 not being able to extend or loop, depth-wise, into and back out of the tissue during initial positioning and use. This is essential in order to be able to excise a portion of tissue during a single pass of the cutting element 40 and is in contradistinction to merely lacerating into a tissue or sealing a tissue. As seen in FIG. 10, adenoid tissue generally forms a mass of tissue with lobes or striations formed therein. The nature of the adenoid tissue A is therefore quite different from that of a blood vessel, for example, which is a generally a tubular form of tissue. With a straight cutting element, or one with a large of a radius of curvature, the cutting element will merely lacerate or cut into the tissue, but will not excise the tissue in a single pass. At least a second pass or second cut is required with such a cutting element.

In addition to securing the end 52 of the cutting element 40, the protuberance 54 serves the function of preventing non-targeted tissue from inadvertently being contacted with the cutting element 40. The protuberance 54 can contact non-targeted tissue, such as the soft palate, while electrical current is being passed through the cutting element 40 during excising of the adenoid tissue, without damage occurring to the non-targeted tissue. The protuberance 54 therefor provides the operator of the cautery forceps 10, as well as the patient, with a degree of protection against inadvertent tissue contact during the surgical procedure. The protuberance 54, in conjunction with the base 50, aids in limiting the depth to which the cutting element 40 can be inserted into the tissue The cutting element 40 is itself preferably in the form of a rigid wire and is perhaps best seen in FIGS. 9 and 11-13. The diameter and exposed length of the wire is selected to achieve a smooth and almost effortless passage of the cutting element 40 through the tissue being excised. For a given length, too large of a diameter wire will make the starting of the cut difficult. Too small of a diameter wire will result in a weaker wire and bending of the wire during the procedure. In a preferred embodiment, the wire of the cutting element is 0.5 mm in diameter and formed of stainless steel. Generally, it has been found that providing a wire of diameter and length, in conjunction with the power supply, sufficient to achieve a power density of between 0.2 and 17.1 W/mm$^2$, will result in acceptable operability of the cautery forceps 10. Exceeding the upper limit of this range, while still resulting in cutting, may produce excessive arcing of the current. Below the lower limit of the power density, ineffective cutting results.

Figure 9:
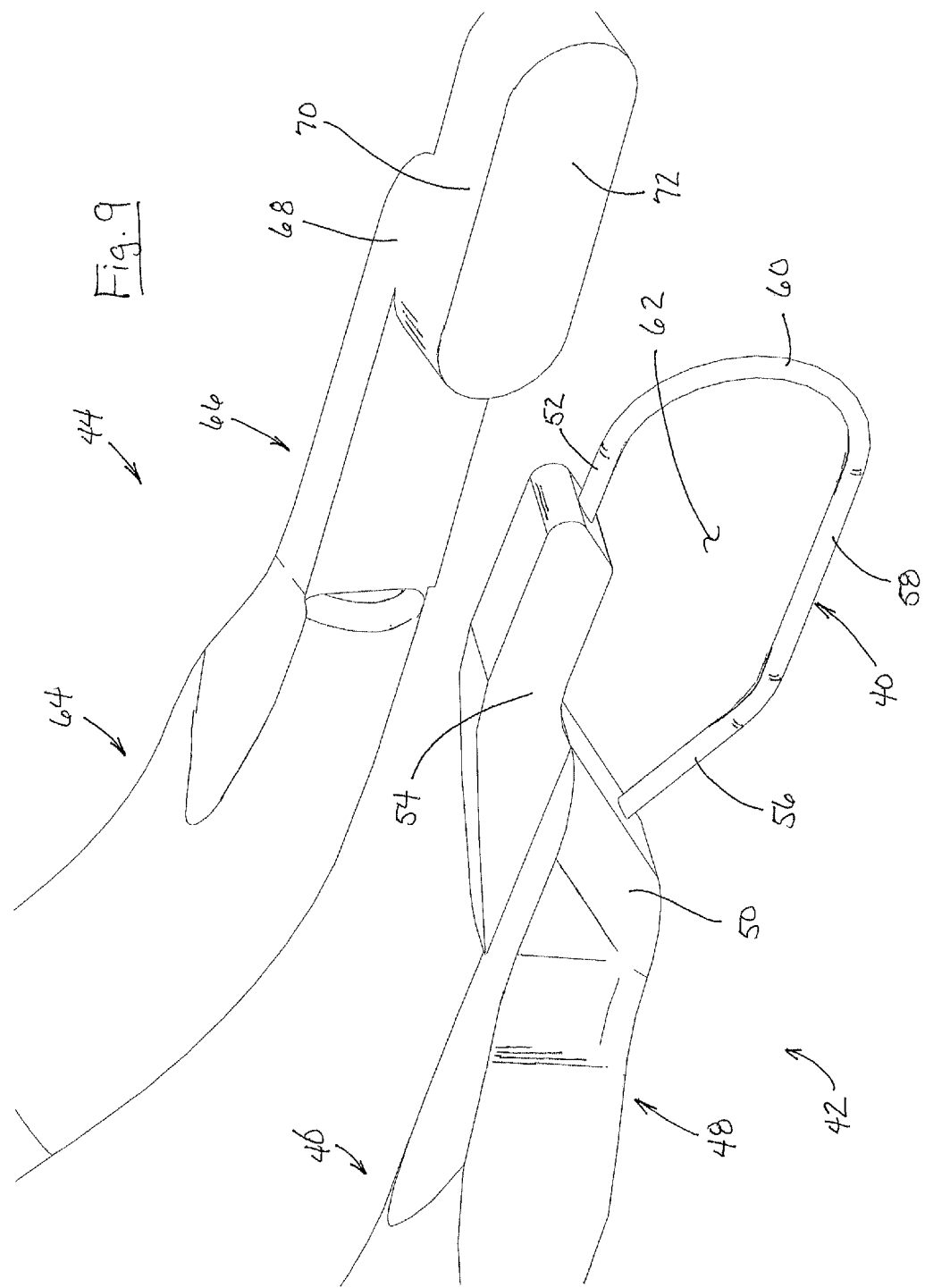
FIG. 9 is an enlarged perspective view of the end effectors of the cautery forceps seen in FIG. 2 in the open position.

As seen in FIG. 9, the cutting element 40 extends from the base 50 of the tip portion 48 via an angled section 56, angled away from the protuberance 54, and thereafter defines a straight section 58. The straight section 58 is generally parallel with a line defined at the end of the curved arm 46. The straight section 58 extends a length that proceeds beyond the end of the protuberance 54, at which point a returnly bent section 60 is formed. The returnly bent section 60 bends toward the protuberance 54, and the end section 62 of the cutting element 40 extends generally parallel to the straight section 58 and also extends into the protuberance 54, thereby defining the loop. The loop itself defines an opening 62 centrally therein.

The resisting end effector 44, on the distal end of the other lever arm 18, likewise includes a curved arm 64 at the end of which is a tip portion 66. The curvature of the arm 64 is such that the arm 64 curves at least in a direction transverse to the relative movement of the lever members 16, similar to the curvature of the arm 46 of the cutting end effector 42.

This tip portion 66 is further seen as having a base 68 to which is attached a pad 70. The pad 70 protrudes or is off-set from the base 68 in a direction toward the cutting element 40 of the other end effector, the cutting end effector 42. The size and shape of the pad 70 is such that the pad 70 can fit within the opening 62 defined by the loop. As seen in FIG. 9, the shape of the pad 70 is oval since the loop has a general oval shape. The shapes, however, need not correspond to one another so long as the pad 70 can fit within the opening 62.

The protruding or off-set of the pad 70 is sufficient to cause the leading surface 72 of the pad 70 to pass through a plane 74 defined by the loop and cutting element 40 when the cautery forceps 10 are fully closed. This closed position of the cautery forceps 10 is seen in FIGS. 4, 5, 11, 12 and 13. As perhaps best seen in FIG. 13, the surface 72 of the pad 70 extends through the plane 74 and is located in a positioned whereby the surface 72 has passed from one side of the plane 74, through the central opening 62, to the other side of the plane 74.

As seen in the figures, the pad 70 is directly opposed to the loop defined by cutting element 40 and protuberance 54. In other words, the pad 70 is generally centered with respect to the central opening 64 of the cutting element 40. It is possible, however, for the pad 70 to oppose the loop while not being directly opposed. Rather, the pad 70 may be off-set or not centered in its position relative to the loop defined by the cutting element 40. Alternatively, the pad 70 may be obliquely oriented relative to the loop. In such instances, only part or none of the pad 70 may pass through central opening 64. The pad 70 instead may contact the cutting element 40 when the cautery forceps 10 are fully closed.

While the shape of the cutting element 40 has been described with particularity in connection with FIG. 9, it is noted that the cutting element 40 may have a variety of shapes. Various possible configurations for the cutting element 40 are shown in FIGS. 14A-14E, and other configurations are also possible. The shape of the pad 70 will likewise vary depending on the shape of the cutting element 40. Accordingly, the pads 70 used in connection with the cutting elements 40 of FIGS. 14A-14E would be correspondingly shaped to pass through the openings and planes defined by those cutting elements 40. Shapes for portions of the cutting element 40 may therefore include, without limitation, round, ovoid, rectangular, triangular, pointed and concave/convex over all or portions of the cutting element 40.

Method of Use

When using the cautery forceps 10, the forceps 10 are first opened and the pad 70 and cutting element 40 are positioned on opposing sides of the adenoid tissue that is to be dissected. In positioning the cautery forceps 10 for use, blunt dissection (the separation of bands of the adenoid tissue without actual cutting of the tissue) is readily performed since the size, shape and orientation of cutting element 40 and pad 70 are conducive to sliding these portions between adjacent the bands the adenoid tissue. Once positioned with the cutting element 40 looping past the surface of the adenoid tissue and back above the surface of the tissue, electrical current is provided to the cutting element 40 and mild pressure is applied by gently squeezing the handles 22 together. In use, the resisting end effector 44 does not need to push adenoid tissue toward the cutting element 40. Rather, it provides a reactionary force that the adenoid tissue bears against as the cutting element 40 moves toward the pad 70. When the proper current and pressure are applied to the cautery electrodes 10, the cutting element 40 will smoothly move through the adenoid tissue being excised. If too much pressure is applied at the start of dissection, there will be excessive contact between the cutting element 40 and the tissue, resulting in the cutting element 40 being buried in the adenoid tissue, preventing passage through the tissue. As the adenoid tissue is being removed, current flows from the cutting element to the adenoid tissue and out of the patient's body at another electrode, which has been attached in a remote location on the patient. With this discharge of current, radio-frequency energy is applied to adenoid tissue, heating the water that resides in the local tissues. The heating of the water in the tissue results in a weakening and/or severing of the tissue, allowing for removal and simultaneous cauterizing of removal site.

To electrically actuate the cautery forceps 10, a switch may be provided in-line with the power cable 14. The switch may be in the form of a hand or foot operated switch, or it may be provided as part of the power source. In a further embodiment, the cutting element 40 might be automatically energized when the end effectors 12 are brought in close proximity of one another. This automatic energizing could be achieved via proximity sensors or limit switches provided as part of the cautery forceps or simply by completing the conductive circuit through the tissue.

The cautery forceps 10 can also be used when closed. In the closed position of the cautery forceps 10, the exposed edge of the cutting element 40 can be used much like the edge of a standard blade cautery. In such an instance, the outer side or edge defined by the cutting element 40 can be used to cauterize.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. An electrosurgical instrument for removal of tissue from a patient, the electrosurgical instrument comprising:
    a pair of lever members;
    an end effector associated with each of the lever members for the removal of tissue, the end effectors being supported by the lever members for relative movement generally toward one another;
    only one of the end effectors including a cutting element that is configured to receive electrical energy from an electrical energy source, the cutting element forming a loop on the end of the end effector and the loop defining a first shape and an opening extending through the end effector;
    the other of the end effectors having a pad provided thereon and projecting in a direction toward the end effector having the cutting element, the pad having a perimeter corresponding in shape to the first shape of the loop, the cutting element and the pad being brought into a position opposing one another during relative movement of the end effectors toward one another with the pad passing into and through the opening of the loop; and
    wherein electrical energy is discharged from the cutting element facilitating dissection and cauterization of the tissue of the patient.

2. The electrosurgical instrument of claim 1, wherein the cutting element is a wire.

3. The electrosurgical instrument of claim 1, wherein the cutting element defines a plurality of radii of curvature.

4. The electrosurgical instrument of claim 1, wherein the loop is a closed loop.

5. The electrosurgical instrument of claim 1, wherein the loop is formed at least in part by the cutting element.

6. The electrosurgical instrument of claim 1, wherein the pad is directly opposed to the loop.

7. The electrosurgical instrument of claim 1, wherein the pad includes a leading surface, in a closed position of the electrosurgical instrument, the leading surface being located on one side of a plane defined by the cutting element and, in an open position of the electrosurgical instrument, the leading surface being located on an opposing side of the plane defined by the cutting element.

8. The electrosurgical instrument of claim 1, wherein the loop is an interrupted loop.

9. The electrosurgical instrument of claim 1, wherein the end effector having the cutting element includes a base and a riser extending off of the base.

10. The electrosurgical instrument of claim 1, wherein the cutting element is configured to produce a power density of between 0.2 and 17.1 $W/mm^2$.

11. The electrosurgical instrument of claim 1, wherein the cutting element has a diameter and a length configured to achieve a power density of between 0.2 and 17.1 $W/mm^2$ in conjunction with a power supply.

12. The electrosurgical instrument of claim 1, wherein the cutting element has a diameter and a length achieving a power density of between 0.2 and 17.1 W/mm² in conjunction with a power supply providing a frequency in the range of 100 KHz to 5 MHz.

13. The electrosurgical instrument of claim 1, wherein the electrosurgical instrument is coupled to a power supply and the power supply can account for impedance variations in the tissue to be removed thereby.

14. The electrosurgical instrument of claim 13, wherein impedance variations are accounted for by one of impedance matching, voltage adjustment, and/or current adjustment.

15. The electrosurgical instrument of claim 1, wherein the pad is not directly opposed to the loop.

16. The electrosurgical instrument of claim 1, wherein the loop extends in a direction transverse to the direction of relative movement of the end effectors toward one another.

17. The electrosurgical instrument of claim 1, wherein the loop is oriented in a plane transverse to the direction of relative movement of the end effectors toward one another.

18. The electrosurgical instrument of claim 1, wherein the perimeter of the pad passes through the opening of the loop.

19. The electrosurgical instrument of claim 1, wherein the pad also defines a face projecting in a direction toward the loop, the face passing into and through the loop with the pad.

20. The electrosurgical instrument of claim 19, wherein the face of the pad is substantially planar.

21. An electrosurgical instrument for removal of tissue from a patient, the electrosurgical instrument comprising:
a pair of lever members;
an end effector associated with each of the lever members for the removal of tissue, the end effectors being supported by the lever members for relative movement generally toward one another;
one of the end effectors including a cutting element that is configured to receive electrical energy from an electrical energy source, the cutting element forming a loop on the end of the end effector, the end effector having the cutting element includes a base and a riser extending off of the base with the riser being laterally offset from the base;
the other of the end effectors including a pad provided thereon, the cutting element and the pad being brought into a position opposing one another during relative movement of the end effectors toward one another; and
wherein electrical energy is discharged from the cutting element facilitating dissection and cauterization of the tissue of the patient.

22. The electrosurgical instrument of claim 21, wherein the loop extends into the riser.

23. The electrosurgical instrument of claim 21, wherein the riser defines a portion of the loop.

24. An electrosurgical instrument for removal of tissue from a patient, the electrosurgical instrument comprising:
a pair of lever members;
an end effector associated with each of the lever members for the removal of tissue, the end effectors being supported by the lever members for relative movement generally toward one another;
only one of the end effectors including a cutting element that is configured to receive electrical energy from an electrical energy source, the cutting element forming a loop on the end of the end effector, the loop defining an opening extending through the end effector and having a first area;
the other of the end effectors including a pad provided thereon and projecting in a direction toward the end effector having the cutting element, the cutting element and the pad being brought into a position opposing one another during relative movement of the end effectors toward one another with the pad passing into and through the opening of the loop, the pad presenting a face toward the loop and the face defining an area that is at least half as large as the first area; and
wherein electrical energy is discharged from the cutting element facilitating dissection and cauterization of the tissue of the patient.

25. The electrosurgical instrument of claim 24, wherein the loop is a closed loop.

26. The electrosurgical instrument of claim 24, wherein the loop is an interrupted loop.

27. The electrosurgical instrument of claim 24, wherein the loop is formed at least in part by the cutting element.

28. The electrosurgical instrument of claim 24, wherein the pad is directly opposed to the loop.

29. The electrosurgical instrument of claim 24, wherein the cutting element is configured to produce a power density of between 0.2 and 17.1 W/mm².

30. The electrosurgical instrument of claim 24, wherein the cutting element has a diameter and a length configured to achieve a power density of between 0.2 and 17.1 W/mm² in conjunction with a power supply.

31. The electrosurgical instrument of claim 24, wherein the cutting element has a diameter and a length achieving a power density of between 0.2 and 17.1 W/mm² in conjunction with a power supply providing a frequency in the range of 100 KHz to 5 MHz.

* * * * *